US00PP11542P

United States Patent [19]

Boeder

[11] Patent Number: Plant 11,542

[45] Date of Patent: Oct. 3, 2000

[54] CHRYSANTHEMUM PLANT NAMED 'PURPLE LUCKY TIME'

[75] Inventor: Mark Boeder, West Wittering, United Kingdom

[73] Assignee: Cleangro Limited, West Sussex, United Kingdom

[21] Appl. No.: 09/133,894

[22] Filed: Aug. 13, 1998

[51] Int. Cl.[7] ..... A01H 5/00

[52] U.S. Cl. ..... Plt./286

[58] Field of Search ..... Plt./286, 297, 298

[56] References Cited

U.S. PATENT DOCUMENTS

P.P. 10,777 2/1999 Wain ..... Plt./297

*Primary Examiner*—Howard J. Locker
*Attorney, Agent, or Firm*—Christie, Parker & Hale, LLP

[57] ABSTRACT

A new variety of chrysanthemum producing red-purple flowers.

1 Drawing Sheet

BACKGROUND OF THE INVENTION

The present invention is directed to a new and distinct variety of chrysanthemum botanically classified as *Dendranthema grandiflora*. The varietal denomination of the new chrysanthemum 'Purple Lucky Time'.

The new variety is a natural single branch sport discovered in a controlled planting of the variety 'Lucky Time'. (U.S. Plant Pat. No. 10,777). The new variety has been asexually reproduced by vegetative cuttings in Ventura County, Calif. and the distinguishing characteristics are retained through successive generations of asexual reproduction.

SUMMARY OF THE INVENTION

'Purple Lucky Time' is pot type chrysanthemum plant variety that produces red-purple flowers having an anemone center about 2.4 cm. and an overall fully expanded bloom of about 6.5 cm. in diameter.

COMPARISON WITH PARENT

The new variety differs in flower color from the parent which produces white/lavender pink flowers with a lavender/pink center.

BRIEF DESCRIPTION OF ILLUSTRATION

The accompanying photograph shows a typical specimen of the new variety with colors being as nearly true as possible with illustrations of this type.

DESCRIPTION OF THE PLANT

The following description of the new variety is of specimens grown in a greenhouse in Ventura County, Calif. in the month of April. 'Purple Lucky Time' has not been observed under all possible environmental conditions. The phenotype may vary with variations in the environment such as temperature, light intensity, day length and cultural conditions. The color designations herein are from The Royal Horticultural Society Colour Chart except where general terms are used.

To produce a commercial product the plants may be pinched once about ten days after planting. It has been observed that the shelf life of 'Purple Lucky Time' is about 24 days with the response time of about 8 weeks. One treatment with grown regulator B9 at 2000 ppm is useful.

Desirable growing conditions include average night temperatures of about 18° to 20° C., and day temperatures of about 20° to 30° C. Plants described are treated with one application of the plant regulator B-9 at a concentration of 1500 ppm.

Plant:

*Habit.*—Upright, herbaceous perennial.
*Height.*—About 30 cm.
*Number of breaks from pinch.*—About 5 to 6.
*Length of lateral branches.*—About 26 cm.
*Stem color.*—Near 137D.

Foliage:

*Leaf arrangement.*—Alternate.
*Number of leaves per lateral branch.*—About 12.
*Leaf size.*— Length: About 7.8 cm. Width: About 4.2 cm.
*Leaf shape.*—Ovate.
*Attachment.*—Petioled.
*Leaf apex.*—Mucronate.
*Base.*—Truncate.
*Margin.*—Palmately lobed.
*Aspect.*—Flat.
*Surface.*—Top: Pubescent. Bottom: Pubescent.
*Midvein color.*—Underside: Near 137D. Upperside: Near 146C.
*Petiole.*—Length: About 1.8 cm. Color: Near 146C.
*Color.*—Mature leaf: Top: Near 137A. Bottom: Near 137B. Young leaf: Top: Near 137B. Bottom: Near 137D.

Bloom:

*Infloresence form.*—Cyme.
*Flower type.*—Anemone-type.
*Number of blooms per branch.*—About 7.
*Anemone center.*—About 2.4 cm.
*Diameter of fully expanded bloom.*—About 6.5 cm.
*Depth of fully expanded bloom.*—About 2 cm.
*Sepal number.*—About 25. Color: Near 137C. Length: About 0.9 cm. Width: About 0.35 cm.
*Peduncle.*—Length: Uppermost peduncle: About 6.5 cm. Lateral peduncle: About 8.2 cm. Habit: Strong, slightly undulating. Surface: Pubescent. Color: Near 138B.
*Flower bud* (*when just showing color*).—Color: Near 59C. Diameter: About 1 cm. Height: About 0.8 cm. Shape: Flattened sphere.

*Ray florets.*—Number per flower: About 32. Texture: Shiny. Shape: Elliptic. Apex: Acute. Base: Tapered. Margin: Entire. Aspect: Ridged, slightly recurved. Length: About 2.8 cm. Width: About 0.8 cm.

*Disc florets.*—Number per flower: About 190. Texture: Shiny. Shape: Cylindric, fluted apex. Length: About 1.4 cm. Width: About 0.3 cm.

*Fragrance.*—Very faint.

Flower color:

*General flower coloration.*—Red-purple ray and disk florets.

*Ray florets, top side.*—Immature: Near 60C. Mature: Near 60B. Fading: Near 58A.

*Ray floret, under side.*—Immature: Near 58A. Mature: Near 58A. Fading: Near 59D.

*Disc florets.*—Immature: Near 60A. Mature: Near 58A. Fading: Near 59D.

*Changes as the flower ages.*—"Anemone" cushion deepens, color fades very slightly.

Reproductive organs:

*Ray florets.*—Pistillate. Stigma shape: 2 branched. Stigma color: Near 7A. Style length: About 0.5 cm. Style color: Near 154A.

*Disc florets.*—Stigma shape: 2 branched. Stigma color: Near 6A. Style Length: About 0.5 cm. Style color: Near 2D. Stamen number: About 5. Anther length: About 0.15 cm. Pollen color: Near 16A. Pollen quantity: Minimal.

What is claimed is:

1. A new and distinct chrysanthemum plant of the variety substantially as herein shown and described.

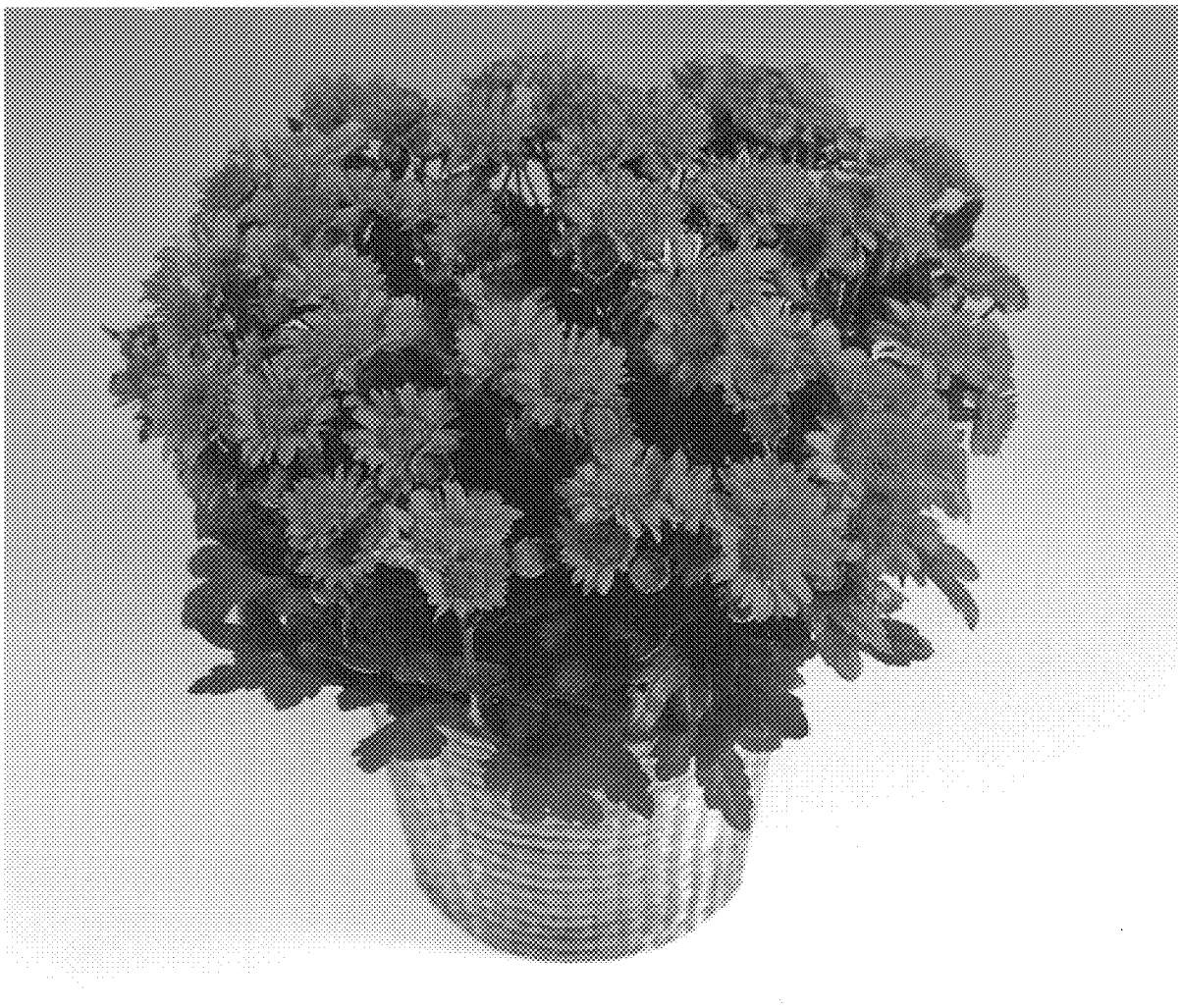

* * * * *